(12) United States Patent
Lerner (10) Patent No.: US 7,720,611 B2
(45) Date of Patent: May 18, 2010

(54) BASELINING AMPLIFICATION DATA

(75) Inventor: Jeffrey Lerner, Oakland, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 1016 days.

(21) Appl. No.: 11/433,183

(22) Filed: May 11, 2006

(65) Prior Publication Data

US 2006/0269947 A1    Nov. 30, 2006

Related U.S. Application Data (60) Provisional application No. 60/680,765, filed on May 13, 2005.

(51) Int. Cl.
- *G06F 19/00* (2006.01)
- *G06F 15/00* (2006.01)
- *G11C 17/00* (2006.01)

(52) U.S. Cl. .............................. 702/19; 365/94; 700/1

(58) Field of Classification Search ....................... None
See application file for complete search history.

(56) References Cited

U.S. PATENT DOCUMENTS 6,783,934 B1    8/2004    McMillan et al.

FOREIGN PATENT DOCUMENTS

| EP | 1 335 028 A | 8/2003 |
|---|---|---|
| WO | WO 03/067215 A | 8/2003 |

OTHER PUBLICATIONS

Extended European Search Report EP 06 75 9657, Dated Aug. 6, 2008.

Tichopad, Ales et al.; "Improving quantitative real-time RT-PCR reproducibility by boosting primer-linked amplification efficiency"; 2002, *Biotechnology Letters*, vol. 24, pp. 2053-2056.

*Primary Examiner*—John S Brusca
(74) *Attorney, Agent, or Firm*—Townsend and Townsend and Crew LLP; David B. Raczkowski (57) ABSTRACT

Methods, apparatus, and systems are provided for processing a data set representing an amplification curve having a baseline portion and a growth portion. Peak objects are generated by taking a derivative of the data set. The first peak object having a value greater than a threshold is identified. An end of the baseline portion from a beginning of the first peak object is estimated.

33 Claims, 7 Drawing Sheets

BASELINING AMPLIFICATION DATA

CROSS-REFERENCES TO RELATED APPLICATIONS

This application claims the benefit of U.S. Provisional Application No. 60/680,765, filed May 13, 2005, entitled "DETERMINATION OF BASELINE END CYCLE IN REAL TIME PCR USING DERIVATIVE PEAK ANALYSIS," which is related to, and concurrently filed with U.S. Provisional Application Ser. No. 60/681,182 entitled "SYSTEMS AND METHODS FOR IDENTIFYING STATISTICALLY FLAT DATA IN A DATA SET", the disclosures of which are incorporated herein by reference in their entirety. The present application is also related to the following commonly-assigned concurrently filed U.S. patent application Ser. No. 11/432,856, entitled "IDENTIFYING STATISTICALLY LINEAR DATA." The respective disclosures of these applications are incorporated herein by reference for all purposes.

BACKGROUND OF THE INVENTION

The present invention relates generally to data processing systems and methods, and more particularly to systems and methods for determining the end of the baseline in an amplification curve, such as in a polymerase chain reaction (PCR).

Many experimental processes exhibit amplification of a quantity. For example, in PCR, the quantity may correspond to the number of parts of a DNA strand that have been replicated, which dramatically increases during an amplification stage or region. PCR data is typically described by a region of linear drifting baseline which is a precursor to exponential growth of PCR amplification. As the consumables are exhausted, the curve turns over and asymptotes. It is desirable to remove the linear drift as much as possible and baseline the signal to zero. For accurate baselining, the beginning and end of the baseline require identifying as accurately as possible. Once this is done, then a linear fit to the points between the begin and end cycles can be subtracted off from the data.

One prior art technique for determining the end of the baseline is as follows. The first pair of points in the curve are selected. For the first point, the first point plus the next three points of the curve are selected for processing. Using these four points, a linear least squares fit is determined and the slope calculated. This process is repeated for the second point. If the change in the two slopes is greater than a fixed number, that is, if the curve turns upward signaling amplification, then the process stops with the end cycle having been determined. If the change in the slops is not greater than the fixed number, the process continues for the next pair of points (e.g., the second and third points in the curve). The process is repeated until a change in slope is greater than the fixed number.

One problem with this approach is that using just four points to define the linear fit is extremely sensitive to small variations in the amplitude of a single point. Spikes or fluctuations due to noisy data will often cause the process to truncate prematurely, resulting in a poor baselining. Moreover, the threshold for the change in slopes is an arbitrary number, which may have to be modified as the data and instrument change. This calibration costs additional time and money. Further, since the algorithm stops when a fixed condition is met, there is no opportunity to analyze the remaining part of the curve to determine if there is a better stopping point.

Therefore it is desirable to provide systems and methods for determining the end cycle of the baseline in an amplification curve that overcome the above and other problems.

BRIEF SUMMARY OF THE INVENTION

The present invention provides systems and methods for determining the end cycle of the baseline in an amplification curve. The data may be received from real-time PCR processes or other processes exhibiting amplification or growth. For example, the PCR curves could be melt curves or fluorescence amplification curves.

According to one exemplary embodiment of the present invention, a module processes an amplification curve by calculating the derivative of the curve and then analyzing peaks in the resulting first derivative. This is termed "Derivative Peak Detection". The module takes a curve and generates a finite set of objects called peak objects having a set of properties.

According to one exemplary embodiment of the present invention, a method of processing a data set representing an amplification curve is provided. The method typically includes receiving a set of data points representing a curve having a baseline portion and a growth portion, and generating a set of one or more peak objects by taking a derivative of at least a portion of the data set. The peak objects occur in the order of the data set. Each peak object has a height related to a local maximum of the derivative. The method also typically includes identifying, in said order, a first peak object having a value greater than a threshold value, and estimating an end of the baseline portion from a beginning of the first such peak object.

In one aspect, the value of the first peak object is the height of the first peak object. In another aspect, the threshold value is determined from a value of one or more of the peak objects. For example, the threshold value may be a mean of the smallest and largest heights in the peak object set.

In one embodiment, before taking the derivative of the amplification curve, the data set is filtered to remove statistically linear data. In another embodiment, before taking the derivative, the data set is filtered to remove data that curves downward or exhibits no amplification.

The method also may further include identifying, and removing from the set of peak objects, peak objects that have a value less than the threshold value. The remaining peak objects may be processed to correct for pathological cases due to noise and fluctuations in the data. Also, the beginning of the first peak object having a value greater than the threshold may be identified as a lower bound for the beginning of the growth portion. The estimate for the end of the baseline portion may be refined by analyzing the data points from the estimated baseline portion toward the growth portion to determine if the data points satisfy linearity. The estimate for the end of the baseline portion may also be refined by comparing values of data points before and after a point within the first peak object to determine if a later peak object is a better estimate to the end of the baseline portion. In one aspect, the average of the values of the data points before the point within the first peak object is compared to at least one average of data points In preferred aspects, the method is implemented in a processor, such as a processor in a stand-alone computer, a network attached computer or a data acquisition device such as a real-time PCR machine. One example of a real-time PCR machine is the iCycler iQ system provided by Bio-Rad Laboratories.

According to another exemplary embodiment of the present invention, an information storage medium having a plurality of instructions adapted to direct an information processing device to perform an operation of processing a data set representing an amplification curve is provided. In one aspect, the information storage medium is a RAM or ROM unit, hard drive, CD, DVD or other portable medium.

According to another exemplary embodiment of the present invention, a PCR detection system is provided. The PCR detection system includes a detector for producing a set of data points representing a curve having a baseline portion and a growth portion and includes logic for processing data to estimate an end of the baseline portion.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION OF THE INVENTION

The present invention provides systems and methods for processing amplification or growth curves to determine characteristics of the growth curve, including an estimate of an end point of a baseline portion. In preferred aspects, the present invention is particularly useful for processing PCR growth or amplification curves to determine an end cycle of the baseline. It should be appreciated, however, that the teachings of the present invention are applicable to processing any data set or curve that exhibits growth or amplification, such as a bacterial growth process.

Figure 1:
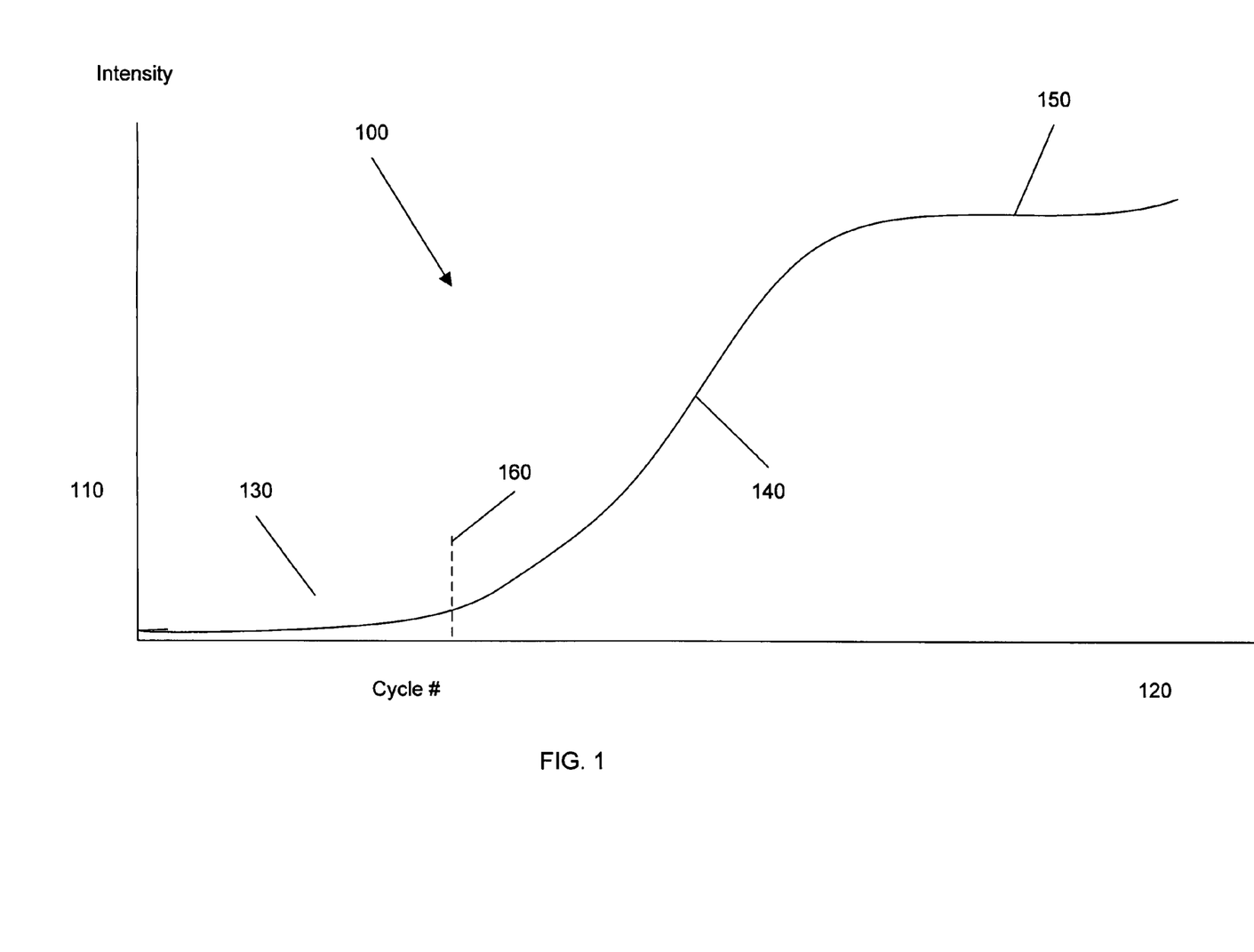
FIG. 1 illustrates an example of a typical PCR amplification curve having a baseline portion.

FIG. 1 shows an example of a PCR curve 100, where intensity values 110 vs. cycle number 120 are plotted for a typical PCR process. The values 110 may be any physical quantity of interest, and the cycle number may be any unit associated with time or number of steps in the process. Such amplification curves typically have a linear portion (region) 130 followed by a growth portion 140 and then by an asymptotic portion 150, as shown in FIG. 1. There also might be additional types of behavior such as downward curving data. A growth portion may have exponential, sigmoidal, high order polynomial, or other type of logistic function or logistic curve that models growth.

To understand the experimental process involved, it is important to identify the position and shape of growth portion 140. For example, in a PCR process, it may be desirable to identify the onset of amplification, which occurs at the end 160 of the baseline portion (linear portion 130). Additionally, the analysis of the shape of growth portion 140 often includes "baselining" or subtracting out linear portion 130 from PCR curve 100.

Figure 2:
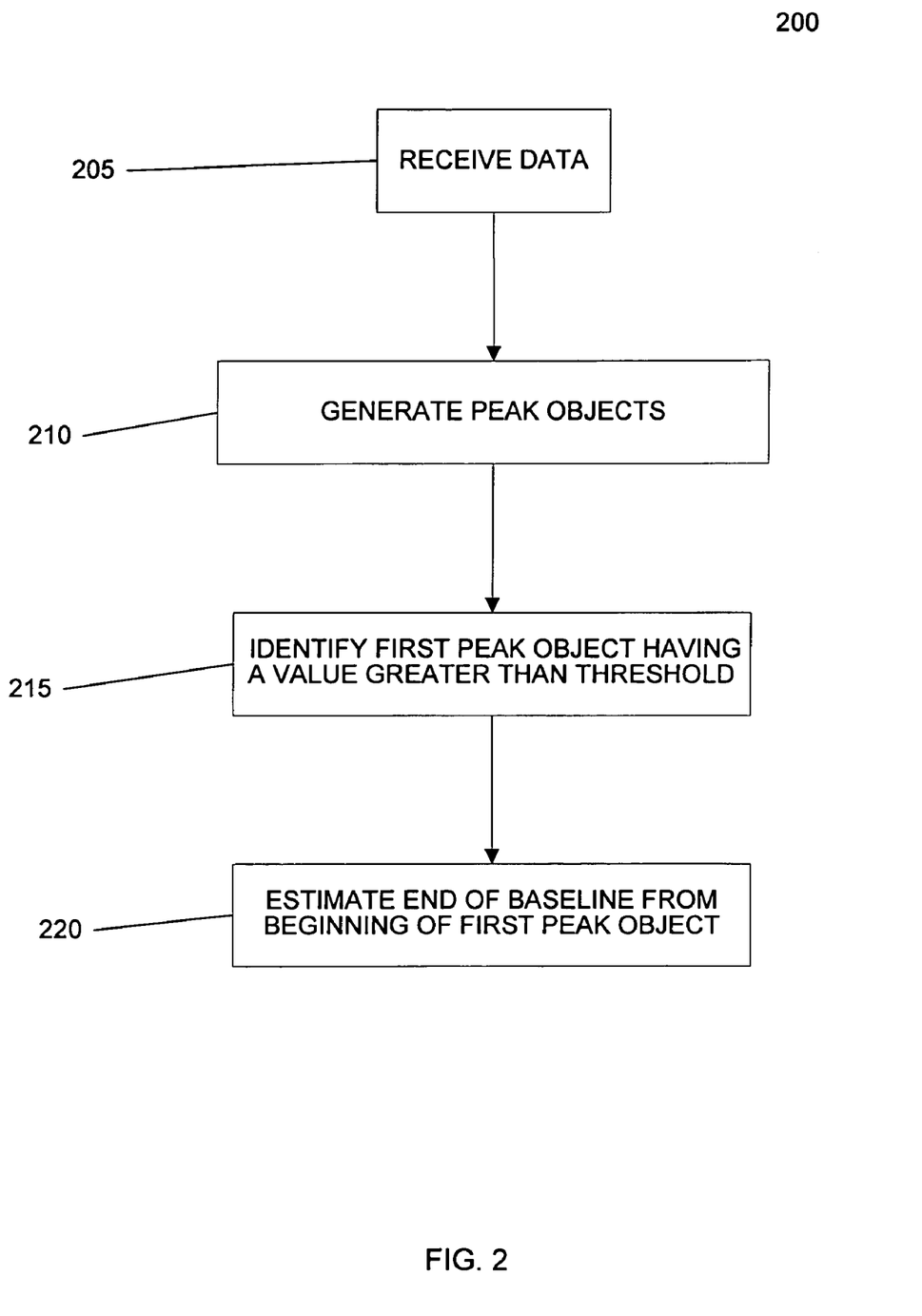
FIG. 2 illustrates a method of processing a data set to determine an end of a baseline portion according to an embodiment of the present invention.

FIG. 2 illustrates a method 200 for processing data according to an embodiment of the present invention. In one aspect, method 200 estimates the end of a baseline portion by taking the derivative of a PCR curve. By analyzing the properties of the derivative curve, a good estimate for the ending point (or ending cycle in PCR systems) of the baseline portion can be determined. The analysis of the properties may include an analysis of the location and size of peaks in the derivative curve. For example, for the derivative of the amplification curve in the exponential portion, there will be a large peak.

In step 205, a set of data points representing a curve having a baseline portion and a growth portion is received. Note that even for devices that produce a constant signal, this data must be broken into data points for analysis. The data set may be received through many mechanisms. For example, the data set may be acquired by a processor (executing instructions) resident in a PCR data acquiring device such as an iCycler iQ device or similar PCR analysis device. The data set may be provided to the processor in real time as the data is being collected, or it may be stored in a memory unit or buffer and provided to the processor after the experiment has been completed. Similarly, the data set may be provided to a separate system such as a desktop computer system via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like to a stand-alone computer system. After the data set has been received or acquired, the data analysis process proceeds as follows.

In step 210, a set of one or more peak objects is generated by taking a derivative of at least a portion of the data set. One or more peak objects may result from taking the derivative. In one embodiment, a derivative peak detection engine is run over the data curve to generate a set of peak objects. The peak objects occur in the same order as the data points. The derivative may be calculated in many ways as would be known to one skilled in the art.

In one embodiment, a functional fit at a data point is obtained by using data points local to that data point. The derivative of that functional fit is then taken to obtain the derivative at that data point. Examples of the functional fit include polynomial fits, such as Savitzky-Golay. The derivative curve may be taken at any number of points along the PCR curve. If a derivative is not taken at a point, then a derivative value at that point may be obtained via interpolation, functional fit, or other suitable methods. Also, derivatives of only part of the curve up to the peak may be taken.

Figure 3A:
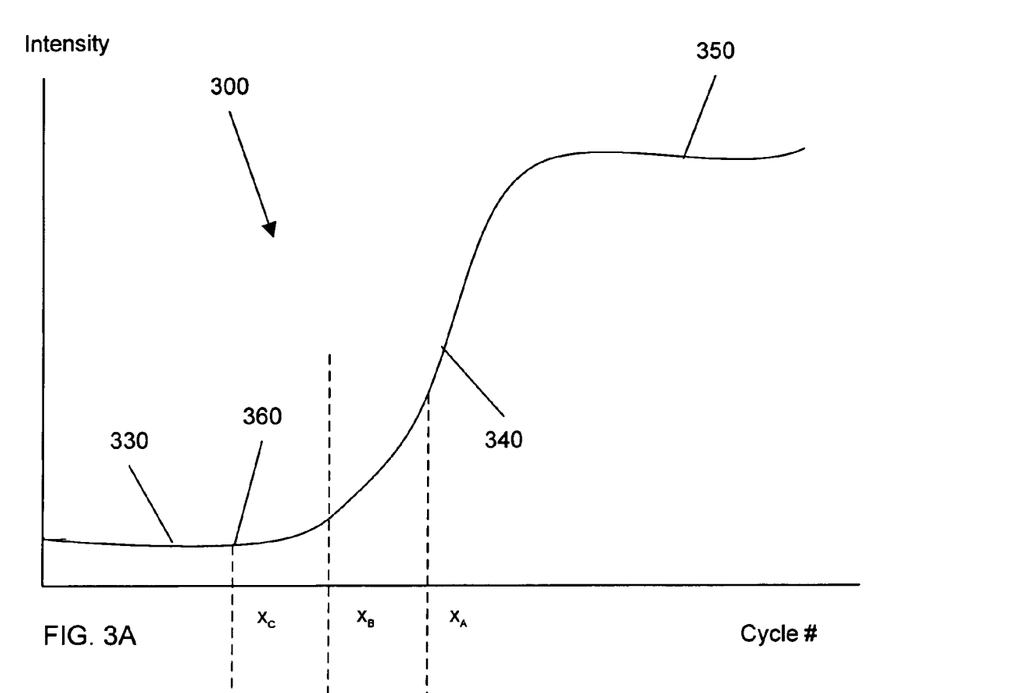
FIG. 3A illustrates an example of a PCR amplification curve having a baseline portion.
Figure 3B:
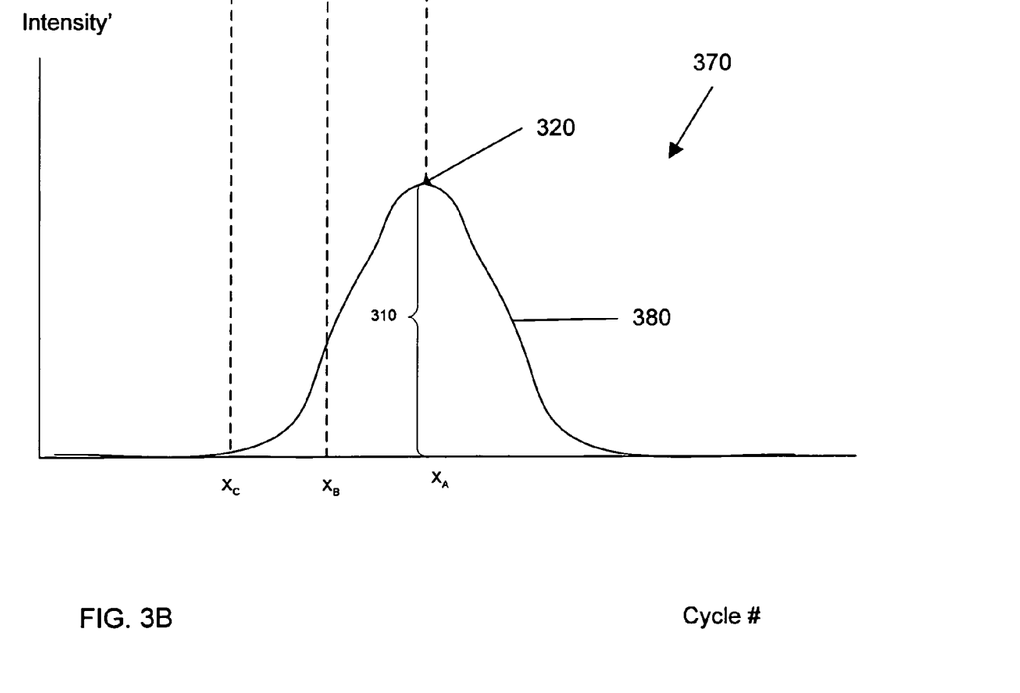
FIG. 3B illustrates an example of a representation of a peak object generated by taking the derivative of an amplification curve, e.g., the curve in FIG. 3A.

FIG. 3B illustrates an example peak object 380 that corresponds to a derivative curve 370 of a growth curve, e.g. PCR curve 300 in FIG. 3A. Peak object 380 has a height 310 corresponding to a local maximum 320 of the derivative. Local maximum 320 corresponds to the point of the highest increase in intensity of CPR curve 300. The use of the term "local maximum" means that another part of the derivative curve, i.e. other peak objects, may have a larger maximum, but around the local area near the top of this peak the local maximum is the largest value. The term "local maximum" is common in functional analysis and the meaning is consistent with the use here.

In FIG. 3B, the location of peak object 380 is defined to occur at its highest point 320. This location occurs at the point of maximum slope of amplification curve 300. This must be to the right of the end cycle for baseline portion 330. In FIGS. 3A and 3B, this point is designated as $x_A$.

The point of maximum slope of the derivative peak curve 370 is the point of maximum curvature of amplification curve 300. This must be to the left of peak object location $x_A$ and to the right of the ending cycle. In FIGS. 3A and 3B, this point is designated as $x_B$.

The start of peak object 380 must be to the left of the point $x_B$ of maximum curvature of amplification curve 300 because the start is to the left of the point $x_B$ of maximum slope of derivative curve 370. In FIGS. 3A and 3B, this point is designated as $x_C$. Thus, location $x_C$ of the start of peak object 380 is bounded to the right by point $x_B$ of maximum curvature of amplification curve 300.

If there is more than one peak object, then a peak list may be created. The peak objects in the list are ordered by their cycle number. Thus, they occur in an order corresponding to an order of the data set. In the prior art method discussed above, only derivative information from the baseline portion and one or two points of the growth portion of the data curve are calculated. Embodiments of the present invention are more robust by including derivative information from other parts of the data curve.

In step 215, the first peak object, in order, having a value greater than a threshold value is identified. The value may be any number related to the peak object. For example, the value may be height 310; an area or width of the peak object; a value that is a set number of cycles away from any location associated with the peak object, such as $x_A$, $x_B$, or $x_C$; or a set percentage of the width from a point of the peak object, or a function of any such value.

In step 220, an end of the baseline portion from a beginning of the first peak object is estimated. The end of the baseline portion may be estimated at the beginning of the peak object, a function of only the beginning, or the beginning may be used as just one parameter in calculating the end of the baseline portion.

For example, since $x_C$ is roughly the end of linear portion 330 before amplification occurs, $x_C$ provides a good estimate for the end cycle of the baseline portion. In general, $x_C$ and $x_A$ provide a good bound for the data in the amplification or exponential portion. For example, however one wishes to analyze a quality or quantity of amplification, such as calculating a threshold value, the quality or quantity must be occurring in the region bound by $x_C$ and $x_A$.

The beginning point $x_C$ of a peak object may be calculated in many ways. For example, the beginning may be set at the local minimum of the derivative curve that is adjacent to the local maximum that defines the height of a peak object.

Figure 4:
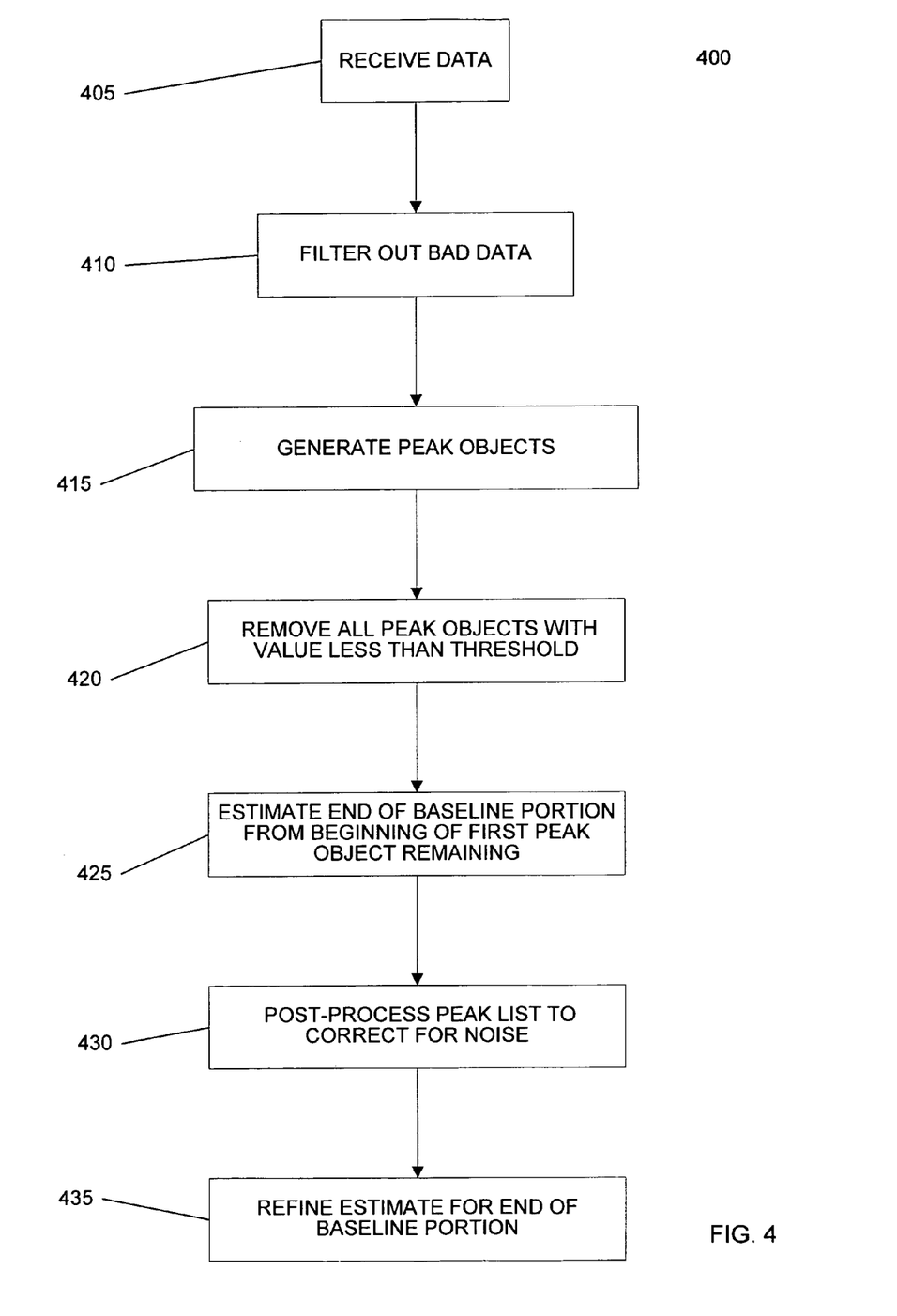
FIG. 4 illustrates another method of processing a data set to determine an end of a baseline portion according to an embodiment of the present invention.
Figure 5A:
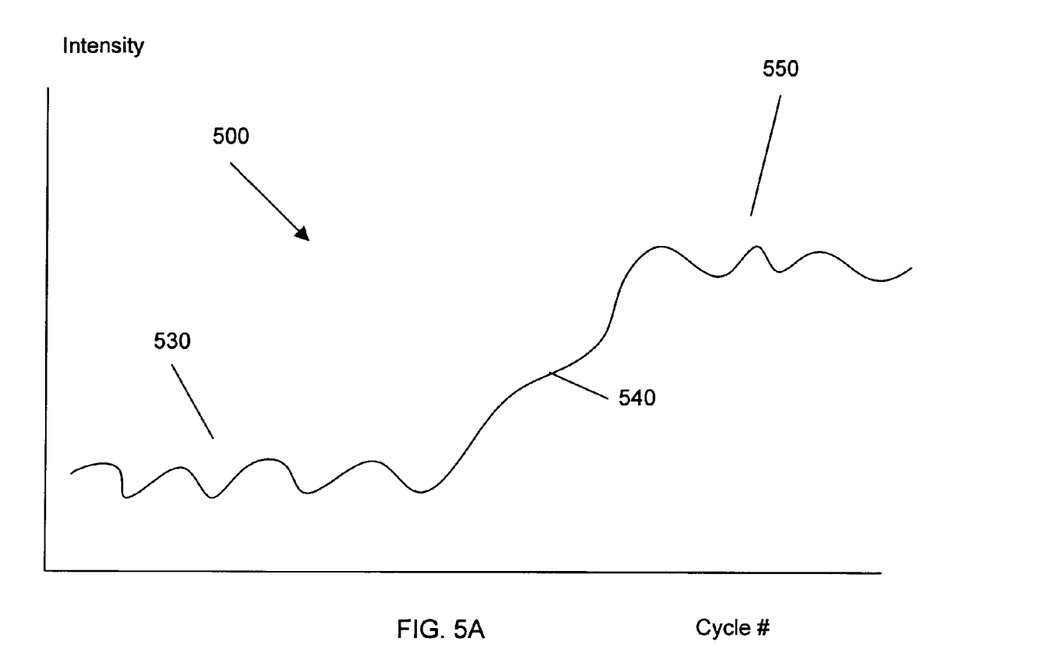
FIG. 5A illustrates an example of a PCR amplification curve having a baseline portion and a noise component.

FIG. 4 illustrates a method 400 for processing data according to an embodiment of the present invention. In step 405, a set of data points representing a curve having a baseline portion and a growth portion is received. Note that even for devices that produce a constant signal, this data must be broken into data points for analysis. Method 400 is particularly useful when the data points include a significant noise component. The noise causes the fluctuations in the data points. FIG. 5A illustrates a real-time PCR curve 500 that exhibits amplification and has a noise component.

In step 410, bad, unwanted or spurious data is filtered out using various techniques. This includes removing data which curves downward exhibiting no amplification. Data displaying statistically linear, noisy behavior, again with no amplification, may also be removed. Co-pending U.S. patent application Ser. No. 11/432,856, filed concurrently with this application, discusses techniques useful for filtering statistically linear (flat) data. Data that does not curve downward and data that is not statistically linear falls through for further processing. Removing these two types of data leaves data which exhibits amplification. Additionally, the data set may be smoothed, e.g. with a low pass filter, to remove at least a portion of a noise component from the data set.

Figure 5B:
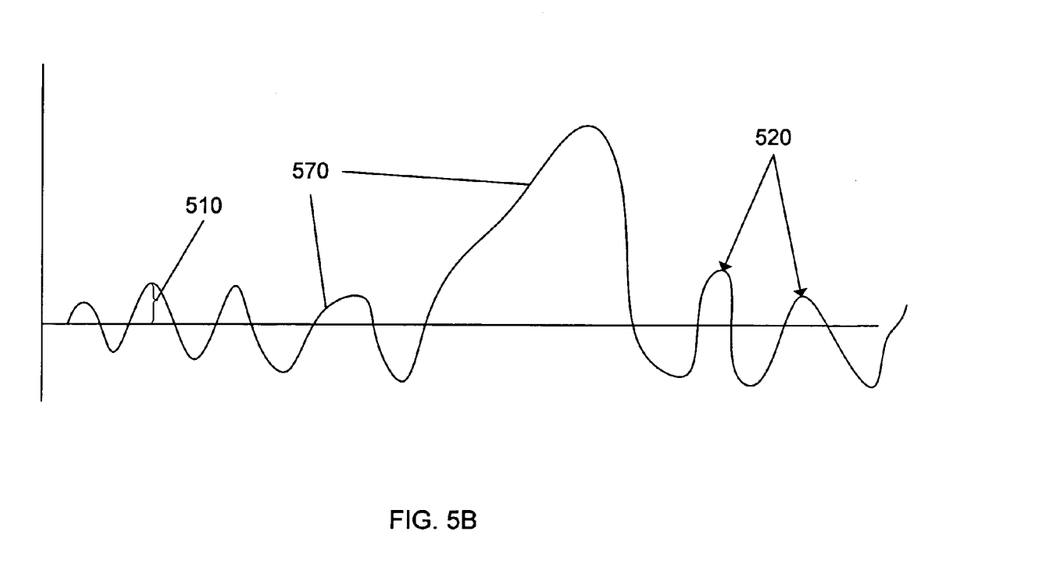
FIG. 5B illustrates an example of a representation of a peak objects generated by taking the derivative of an amplification curve, e.g., the curve in FIG. 5A.

In step 415, a set of one or more peak objects is generated by taking a derivative of at least a portion of the data set. A derivative peak detection engine may be run over the (filtered or non-filtered) data curve to generate a set of peak objects. For example, FIG. 5A shows an example of a PCR curve 500 having a linear portion (region) 530 followed by a growth portion 540 and then by an asymptotic portion 550. FIG. 5B illustrates a derivative curve 560 of a growth curve, e.g. PCR curve 500. Within derivative curve 560 there are multiple peak objects 570. Each peak object 570 has a height 510 corresponding to a local maximum 520 of the derivative curve 560.

If there is more than one peak object as in FIG. 5B, then a peak list may be created. The peak objects in the list are ordered by their cycle number. Thus, they occur in an order corresponding to an order of the data set. In one embodiment, the full set of derivative peaks for the entire amplification data curve is generated. In other embodiments, less than the full set of derivative peaks may be generated.

In step 420, all peaks having a value less than a threshold value are discarded or removed. In one embodiment, a filtered peak object list is generated. As can be seen in FIG. 5A of PCR curve 500, real data includes noise and variations, which may give rise to small peaks, such as in FIG. 5B. Thus, a filter may be run over the peak object set to remove all of the smaller peaks. In one aspect, the threshold value is the mean of the smallest and largest peak heights. Other functions of these peaks may be used. In other embodiments, the values of other peaks and functions of these values may be used.

In step 425, an end of the baseline portion is estimated from a beginning of the first peak object occurring in the filtered list. The starting cycle of the first (earliest) occurring peak in the filtered peak set provides a very good estimate for the ending cycle of the baseline. For clean data, this has been found to be an excellent guess. This process works whether the baseline is horizontal or has a positive slope, since the linear nature of the baseline just contributes a constant to the derivative curve, which has no effect upon peaks.

In step 430, the filtered peak list is post-processed to correct for special or pathological cases that may arise, e.g. due to noise, fluctuations in the data, special peaks, and configuration cases. This refines the guess for the peak defining the end cycle.

Figure 6:
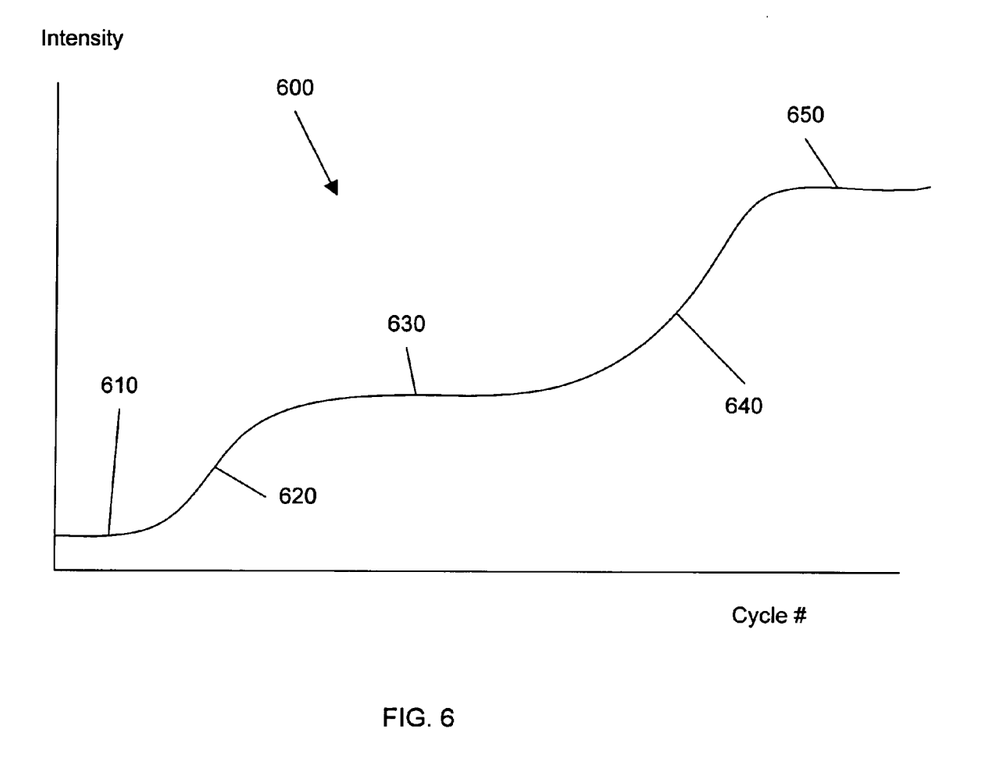
FIG. 6 illustrates an example of a PCR amplification curve having a baseline portion and a noise component and exhibiting pathological behavior.

For example, FIG. 6 shows a PCR curve 600 that may need refinement. Amplification curve 600 has a first linear portion 610 followed by a first growth portion 620, and then by a first asymptotic portion 630, as shown in FIG. 6. Growth portion 630 corresponds to the linear portion of a second growth portion 640, which is followed by a second asymptotic portion 650.

In one embodiment during post-processing, first growth portion 620 is used to define a begin cycle and second growth portion 640 is used to define an end cycle. This might be done when the total change in intensity value from first growth portion 620 is less than the total change in intensity value from second growth portion 640. The begin and end cycles are then used to define a baseline portion that is removed from second growth portion 640.

In step 435, once a good guess for the end peak has been obtained, the estimate for the ending cycle can be further refined. In one embodiment, the refinement is accomplished by scanning the estimated baseline portion toward the growth portion. The scanning or analyzing of the baseline portion may include testing data points to the right of the estimated ending cycle for the baseline region to determine if these data points exhibit a better fit to linearity, or if they exhibit any linearity at all.

In another embodiment, the change in the intensity values of the data points of a PCR curve on either side of peak objects are examined to determine a better ending cycle. For example, if the intensity values before the estimated end of the baseline portion are not significantly lower than the intensity values in cycles after, then a later peak object may be chosen to define the end of the baseline portion. In one embodiment, the intensity values before the first peak object are averaged, and this average is compared to an average of values between the first and second peak objects. Values, and averages thereof, between other peak objects may also be compared.

The prior art method discussed above uses scanning from left to right looking for the first failure point of a slope comparison method. That method uses exclusively local properties and stops without knowing anything about the properties of the curve that occur later than its stop point. Embodiments of the present invention are more robust by including derivative information from other parts of the data curve.

In one embodiment, the whole amplification curve is mapped onto a set of numbers, and the whole data set is analyzed to determine the best estimate for the whole amplification curve. Thus, in this embodiment, while this embodiment uses local (derivative) properties of the amplification curve to define peaks, the entire set of peaks may be analyzed to find the best end cycle. For example, the first filtered peak is used as a first estimate, and later peaks may be checked to determine whether, due to noise or other fluctuations in the data, there may be a better estimate. In this sense, the amplification curve can be analyzed globally, which is preferably done during the post-processing code to handle special cases.

In certain aspects, code and instructions for controlling a processor to implement the data processing techniques of the present invention is stored on a computer-readable medium such as a RAM or ROM unit, hard drive, CD, DVD or other portable medium.

Figure 7:
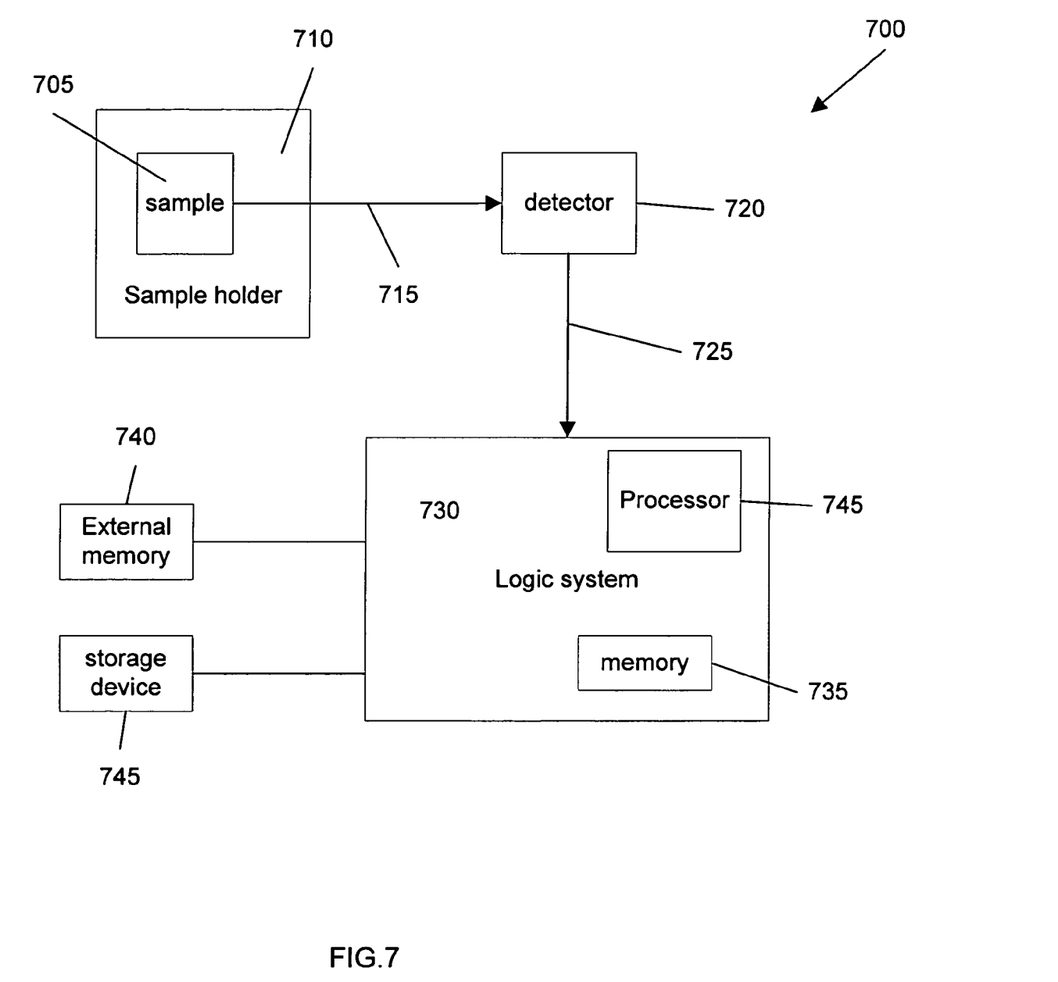
FIG. 7 illustrates a system that processes real-time PCR data according to an embodiment of the present invention.

FIG. 7 illustrates a system 700 according to one embodiment of the present invention. The system as shown includes a sample 705, such as bacteria or DNA, within a sample holder 710. A physical characteristic 715, such as a fluorescence intensity value, from the sample is detected by detector 720. A signal 725, including a noise component, is sent from detector 720 to logic system 730. The data from signal 725 may be stored in a local memory 735 or an external memory 740 or storage device 745. In one embodiment, an analog to digital converter converts an analog signal to digital form.

Logic system 730 may be, or may include, a computer system, ASIC, microprocessor, etc. It may also include or be coupled with a display (e.g., monitor, LED display, etc.) and a user input device (e.g., mouse, keyboard, buttons, etc.). Logic system 730 and the other components may be part of a stand alone or network connected computer system, or they may be directly attached to or incorporated in a thermal cycler device. Logic system 730 may also include optimization software that executes in a processor 750.

According to one embodiment, logic system 730 includes instructions for processing data and identifying statistically flat data. The instructions are preferably downloaded and stored in a memory modules 735, 740, or 745 (e.g., hard drive or other memory such as a local or attached RAM or ROM), although the instructions can be provided on any software storage medium such as a floppy disk, CD, DVD, etc. It should be understood that computer code for implementing aspects of the present invention can be implemented in a variety of coding languages such as C, C++, Java, Visual Basic, and others, or any scripting language, such as VBScript, JavaScript, Perl or markup languages such as XML. In addition, a variety of languages and protocols can be used in the external and internal storage and transmission of data and commands according to aspects of the present invention.

It will be appreciated that the process described herein is illustrative and that variations and modifications are possible. Steps described as sequential may be executed in parallel, order of steps may be varied, and steps may be modified or combined.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of processing a data set representing an amplification curve, the method comprising:
receiving a set of data points representing a curve having a baseline portion and a growth portion;
generating a set of one or more peak objects by taking a derivative of at least a portion of the data set, wherein each peak object has a height related to a local maximum of the derivative, wherein the peak objects occur in an order corresponding to an order of the data set;
identifying, in said order, a first peak object having a value greater than a threshold value; and
estimating an end of the baseline portion from a beginning of the first peak object, wherein the method is implemented using a processor.

2. The method of claim 1, wherein the value of the first peak object is the height of the first peak object.

3. The method of claim 1, wherein the threshold value is determined from a value of one or more of the peak objects.

4. The method of claim 3, wherein the threshold value is a mean of the smallest and largest heights in the peak object set.

5. The method of claim 1, further comprising:
before taking the derivative, filtering the data set to remove statistically linear data.

6. The method of claim 1, further comprising:
before taking the derivative, filtering the data set to remove data that curves downward or exhibits no amplification.

7. The method of claim 1, further comprising identifying, and removing from the set of peak objects, peak objects that have a value less than the threshold value.

8. The method of claim 7, wherein the first peak object identifies a lower bound for the beginning of the growth portion.

9. The method of claim 8, further comprising refining the estimate for the end of the baseline portion, by:
analyzing the data points from the estimated baseline portion toward the growth portion to determine if the data points satisfy linearity.

10. The method of claim 8, further comprising refining the estimate for the end of the baseline portion, by:
comparing values of data points before and after a point within the first peak object to determine if a later peak object is a better estimate to the end of the baseline portion.

11. The method of claim 10, wherein the average of the values of the data points before the point within the first peak object is compared to at least one average of data points.

12. The method of claim 7, further comprising processing the remaining peak objects to correct for noise and fluctuations in the data.

13. The method of claim 1, wherein the processor is integrated in one of a stand alone computer system, a networked computer system or a real-time PCR machine.

14. The method of claim 1, wherein the amplification curve represents a real-time PCR data curve.

15. An information storage medium having a plurality of instructions adapted to direct an information processing device to perform an operation of processing a data set representing an amplification curve, the operation comprising the steps of:
receiving a set of data points representing a curve having a baseline portion and a growth portion;
generating a set of one or more peak objects by taking a derivative of at least a portion of the data set, wherein each peak object has a height related to a local maximum of the derivative, wherein the peak objects occur in an order corresponding to an order of the data set;
identifying, in said order, the first peak object having a value greater than a threshold value; and
estimating an end of the baseline portion from a beginning of the first peak object.

16. The information storage medium of claim 15, wherein the value of the first peak object is the height of the first peak object.

17. The information storage medium of claim 15, wherein the threshold value is determined from a value of one or more of the peak objects.

18. The information storage medium of claim 15, wherein the operation further comprises:
before taking the derivative, filtering the data set to remove statistically linear data.

19. The information storage medium of claim 15, wherein the operation further comprises:
before taking the derivative, filtering the data set to remove data that curves downward or exhibits no amplification.

20. The information storage medium of claim 15, wherein the operation further comprises:
identifying, and removing from the set of peak objects, peak objects that have a value less than the threshold value.

21. The information storage medium of claim 20, wherein the first peak object identifies a lower bound for the beginning of the growth portion.

22. The information storage medium of claim 21, wherein the operation further comprises refining the estimate for the end of the baseline portion.

23. The information storage medium of claim 20, wherein the operation further comprises processing the remaining peak objects to correct for noise and fluctuations in the data.

24. A PCR detection system comprising:
a detector for producing a set of data points representing a curve having a baseline portion and a growth portion; and
logic for processing a data set representing an amplification curve to estimate an end of the baseline portion, by:
generating a set of one or more peak objects by taking a derivative of at least a portion of the data set, wherein each peak object has a height related to a local maximum of the derivative, wherein the peak objects occur in an order corresponding to an order of the data set;
identifying, in said order, the first peak object having a value greater than a threshold value; and
estimating an end of the baseline portion from a beginning of the first peak object.

25. The PCR detection system of claim 24, wherein the value of the first peak object is the height of the first peak object.

26. The PCR detection system of claim 24, wherein the threshold value is determined from a value of one or more of the peak objects.

27. The PCR detection system of claim 24, wherein the operation further comprises:
before taking the derivative, filtering the data set to remove statistically linear data.

28. The PCR detection system of claim 24, wherein the operation further comprises:
before taking the derivative, filtering the data set to remove data that curves downward or exhibits no amplification.

29. The PCR detection system of claim 24, wherein the operation further comprises:
identifying, and removing from the set of peak objects, peak objects that have a value less than the threshold value.

30. The PCR detection system of claim 29, wherein the first peak object identifies a lower bound for the beginning of the growth portion.

31. The PCR detection system of claim 30, wherein the operation further comprises refining the estimate for the end of the baseline portion.

32. The PCR detection system of claim 29, wherein the operation further comprises processing the remaining peak objects to correct for noise and fluctuations in the data.

33. The method of claim 1, wherein each data point represents a physical quantity of a substance during an amplification process.

* * * * *